United States Patent
Kwetkat et al.

[11] Patent Number: 6,121,482
[45] Date of Patent: *Sep. 19, 2000

[54] AMPHIPHILIC COMPOUNDS WITH AT LEAST TWO HYDROPHILIC AND AT LEAST TWO HYDROPHOBIC GROUPS BASED ON DICARBOXAMIDES

[75] Inventors: Klaus Kwetkat, Lünen; Herbert Koch, Dorsten; Wulf Ruback, Dülmen, all of Germany

[73] Assignee: Huels Aktiengesellschaft, Marl, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/894,159
[22] PCT Filed: Nov. 17, 1995
[86] PCT No.: PCT/EP95/04530
 § 371 Date: Aug. 18, 1997
 § 102(e) Date: Aug. 18, 1997
[87] PCT Pub. No.: WO96/25388
 PCT Pub. Date: Aug. 22, 1996

[30] Foreign Application Priority Data

Feb. 17, 1995 [DE] Germany ............ 195 05 368

[51] Int. Cl.$^7$ .................. C07C 229/00; B01D 17/04
[52] U.S. Cl. .............. 560/169; 252/174.21; 252/174.22; 252/550; 510/119; 510/130; 510/276; 510/437; 558/30; 558/166; 562/47; 564/153
[58] Field of Search ............. 252/174.21, 174.22, 252/550; 564/753; 560/169; 562/47; 558/166.3; 510/119, 130, 276, 437

[56] References Cited

U.S. PATENT DOCUMENTS 5,160,450 11/1992 Okahara et al. ............. 252/174.21

FOREIGN PATENT DOCUMENTS 0 037 996 10/1981 European Pat. Off. .
0689-0794-0 6/1998 WIPO .

OTHER PUBLICATIONS

Chemical Abstracts, AN 92 189237, JP 04 124165, Apr. 24, 1992.
R. Zana, et al., Langmuir, American Chemical Society, vol. 7, No. 6, pp. 1072–1075, "Alkanediyl–A,W–Bis(Dimethylalkylammonium Bromide) Surfactants. 1. Effects of the Spacer Chain Length on the Critical Micelle Concentration and Micelle Ionization Degree", 1991.

R. Zana, et al., Nature, vol. 362, pp. 228–230, "Dependence of Aggregate Morphology on Structure of Dimeric Surfactants", Mar. 18, 1993.

E. Alami, et al., Langmuir, American Chemical Society, vol. 9, No. 6, pp. 1465–1467, "Alkanediyl–A,W–Bis(Dimethylalkylammonium Bromide) Surfactants. 3. Behavior at the Air–Water Interface", 1993.

A. Behler, et al., Chemieprodukte, vol. 116, No. 2, pp. 60–67, New Thickening Agents for Surfactants, Feb. 7, 1990.

A. Khatory, et al., Langmuir, American Chemical Society, vol. 9, No. 6, pp. 1456–1464, "Linear and Nonlinear Viscoelasticity of Semidilute Solutions of Wormlike Micelles at High Salt Content", 1993.

D. Balzer, Tenside Surf. Det., vol. 28, No. 6, pp. 419–427, "Alkylpolyglucosides, Their Physico–Chemical Properties and Their Uses", 1991.

Dieter Balzer, Langmuir, American Chemical Society, vol. 9, No. 12, pp. 3375–3384, "Cloud Point Phenomena in the Phase Behavior of Alkyl Polyglucosides in Water", 1993.

Micich et al, Jaocs. vol. 65, No. 5, 1988.

*Primary Examiner*—Shailendra Kumar
*Attorney, Agent, or Firm*—Oblon, Spivak, McClelland, Maier & Neustadt, P.C.

[57] ABSTRACT

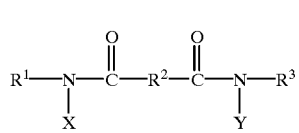

(I)

The invention concerns amphiphilic compounds of general formula (I), in which $R^1$ and $R^3$ each represent a $C_1$–$C_{22}$ hydrocarbon residue, $R^2$ is a spacer and X and Y are functional groups. The proposed compounds have at least two hydrophilic and at least two hydrophobic groups based on dicarboxylic acid diamides. The amphiphilic compounds according to the invention are mostly surface-active and are especially suitable for use as emulsifiers, demulsifies, detergents, dispergents and hydrotropic agents in industry and households, for example, in the treatment of metals, ore processing, surface finishing, washing, cleaning, cosmetics, medicine and food processing and preparation.

11 Claims, No Drawings

AMPHIPHILIC COMPOUNDS WITH AT LEAST TWO HYDROPHILIC AND AT LEAST TWO HYDROPHOBIC GROUPS BASED ON DICARBOXAMIDES

This application is a 371 of PCT/EP95/04530, filed Nov. 17, 1995.

The invention relates to amphiphilic compounds with at least two hydrophilic and at least two hydrophobic groups based on diamides.

A wide variety of anionic, cationic or nonionic and zwitterionic compounds are known as amphiphilic substances. By far the most of these substances consist of a hydrophilic head group and at least one hydrophobic part.

With the amphiphilic substances there is a need, for ecological reasons, for example concerning the reduction in the cost of packaging and transport, to achieve an increasingly greater effect per mass of substance employed. Since optimization by mixing amphiphilic substances produces only very limited advances, novel amphiphilic substances with greater efficiency are required. It is therefore necessary in particular to find substances with lower critical micelle concentrations and/or lower surface and interfacial tensions in order to be able to reduce markedly the amounts of active substance.

Initial approaches to a solution in this direction by doubling one part of the structure (hydrophilic head group, hydrophobic group) have already been disclosed. Thus, cationic surface-active compounds can be obtained by adding long-chain alkyl halides onto permethylated alkylenediamines [R. Zana, M. Benrraou, R. Rueff, Langmuir, 7 (1991) 1072: R. Zana, Y. Talmon, Nature, 362 (1993) 228; E. Alami, G. Beinert, P. Marie, R. Zana, Langmuir, 9 (1993) 1465].

Anionic surface-active compounds with at least two hydrophilic and at least two hydrophobic groups have to date been prepared only on the basis of diglycidyl ethers (U.S. Pat. No. 5,160,450, JP 01 304 033, JP 4 124 165). However, diglycidyl ethers are regarded as toxicologically objectionable and are rather costly. Furthermore, epichlorohydrin is used for their preparation, which leads to large amounts of residues so that these compounds are no longer in accord with the times from the ecotoxicological and economic viewpoints.

The object therefore was to find amphiphilic compounds which have at least two hydrophilic and at least two hydrophobic groups, the amphiphilic compounds having a very high efficiency relative to the amount used, and which furthermore can be prepared from raw materials which are easily available industrially and without large amounts of unwanted by-products being formed.

The object is achieved according to the invention by amphiphilic diamides whose basic skeleton can be prepared from dicarboxylic acids or their esters and amines. The corresponding di- or oligoamides can be alkoxylated. These nonionic amphiphilic compounds can be converted into anionic amphiphilic compounds by, for example, reacting the abovementioned compounds with $SO_3$/inert gas (or oleum chlorosulfonic acid or sulfamic acid), with polyphosphoric acid, with a haloacetic acid, with a sultone, with maleic anhydride and sodium bisulfite or with a taurine and, in each case, subsequently neutralizing.

The amphiphilic compounds according to the invention are therefore compounds of the general formula I

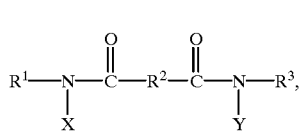

where $R^1$, $R^2$, $R^3$, X and Y in formula I have the meanings described below:

$R^1$ and $R^3$ are, independently of one another, an unbranched or branched, saturated or unsaturated hydrocarbon radical with 1 to 22, preferably 7 to 17, carbon atoms.

Specific substituents $R^1$ and $R^3$ which may be mentioned are the radicals methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl and their branched-chain isomers, and the corresponding singly, doubly or triply unsaturated radicals.

$R^2$ is a spacer consisting of an unbranched or branched chain with 2 to 100 carbon atoms, which contains 0 to 20 oxygen and/or 0 to 20 nitrogen atoms and/or 0 to 4 sulfur atoms and/or 0 to 3 phosphorus atoms, and which has 0 to 20 functional side groups.

The spacer $R^2$ is, in particular, unbranched or branched alkylene chains of the formula II as basic skeleton

with a=2 to 18, preferably a=3 to 6;

unbranched or branched alkenylene chains of the formula III as basic skeleton

with b+c=2 to 16, where b and c are each greater than zero;

unbranched or branched alkynylene chains of the formula IV as basic skeleton

with d+e=2 to 16, where d and e are each greater than zero, and where in the compounds according to formulae II to IV the spacer contains at any desired point in the chain additionally 0 to 4 carbonyl, carboxyl, amino or acylamino groups;

alicycles according to the formula V

with f and g = each 1 to 6 or according to formula VI

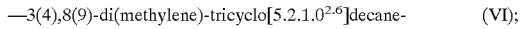

unsubstituted or substituted aromatics according to the formula VII

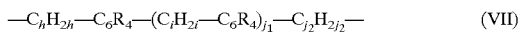

or according to the formula VIII

with h, j, $j_1$ and $j_2$ = each 0 to 8 and i=1 to 8 and with R=independently of one another in each case H or $C_1$- to $C_4$-alkyl;

a chain with 0 to 20 functional side groups, where the functional side groups consist of amino, acylamino, carbonyl, carboxyl or hydroxyl groups, and/or 0 to 4 rings, which are isolated or fused.

Furthermore, the spacer $R^2$ contains in each case 0 to 20, preferably 1 to 12, oxygen and/or nitrogen atoms, 0 to 4 sulfur atoms and 0 to 3 phosphorus atoms.

$R^2$ thus furthermore has in particular the meaning of a compound according to the formula IX

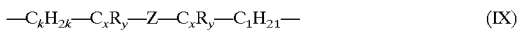  (IX)

with k and l = each 0 to 8, x=6 and y=4 or x=10 and y=6 or x=14 and y=8, and Z=O, CO, NH, $NR^1$, N—C(O)$R^1$, $SO_2$, where $R^1$ is a hydrocarbon radical with 1 to 22 carbon atoms and R are, independently of one another, in each case H or $C_1$- to $C_4$-alkyl;

of a compound according to the formula X

  (X)

m=1 to 4, n=2 to 4, p=1 to 20, preferably p=1 to 6 and q=1 to 4, where mixed alkoxide units may also occur and then the sequence of the alkoxide unit is arbitrary;

of a compound according to the formula XI

  (XI)

or according to the formula XII

  (XII)

or according to the formula XIII

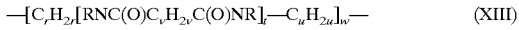  (XIII)

or according to the formula XIV.0

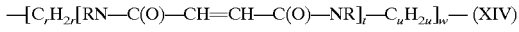  (XIV)

or according to the formula XV

  (XV)

with r=2 to 4, s=2 to 4, t=1 to 20, preferably t=1 to 4, u=2 to 4, v=0 to 12, w=1 to 6, x=6 and y=4 or x=10 and y=6 or x=14 and y=8 with R=independently of one another in each case H or $C_1$- to $C_4$-alkyl.

X and Y are, independently of one another, functional groups in particular substituents of the formula XVI

  (XVI)

with α=0 to 50, preferably α=10 to 30, β=0 to 60, preferably β=20 to 40,
and α+β=1 to 100, preferably α+β=10 to 50, where $R^2$ is not $C_2H_4$ when β=0.
and where with mixed alkoxides the alkoxide units are incorporated randomly or blockwise and the sequence is arbitrary,
or substituents of the formula XVII

  (XVII)

with in each case
γ=0 to 20, preferably γ=0 to 8,
δ=0 to 20, preferably δ=0 to 12,
and γ+δ=1 to 40, preferably γ+δ=5 to 20, where RF is a functional radical —$CH_2$—COOM, —$SO_3M$, —P(O)(OM)$_2$,
—O—C(O)—$C_2H_3(SO_3M)$—$CO_2M'$ or —$C_2H_4$—$SO_3M$
with M, M'=alkali metal, ammonium, alkanolammonium or ½ alkaline earth metal, or substituents of the formula XVIII

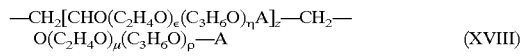  (XVIII)

with z=3 to 6, preferably z=4 and ϵ or $\mu$=0 to 30, preferably ϵ or $\mu$=0 to 10, and η or ρ=0 to 30, preferably η or ρ=0 to 10, and where the alkoxide units are likewise incorporated randomly or blockwise and the sequence is arbitrary and where A is H or FR.

The degree of alkoxylation is in each case an average and can assume any desired, including non-integral, value within the stated limits.

The amphiphilic compounds according to the invention are usually distinguished by extremely low critical micelle concentrations (CMC) and very low surface and interfacial tensions (for example in the presence of paraffin), which must be ascribed to their special structure—at least two hydrophilic groups and at least two hydrophobic groups. Furthermore, most of them display a rather high hydrophilic suspension capacity which is about halfway between that of conventional surfactants and that of pentasodium tripolyphosphate. Some of these compounds are extremely rapid wetting agents.

The amphiphilic compounds according to this invention are particularly suitable as emulsifiers, demulsifiers, detergents, dispersants and hydrotropes in industry and domestically, for example in the areas of metal processing, ore production, surface treatment, washing and cleaning, cosmetics, medicine and foodstuff processing and preparation.

In these cases they can be combined with all customary anionic, nonionic, cationic and ampholytic surface-active substances. Examples of nonionic surface-active substances which can be used for a combination and which may be mentioned are: fatty acid glycerides, fatty acid polyglycerides, fatty acid esters, ethoxylates of higher alcohols, polyoxyethylene fatty acid glycerides, polyoxyethylene/propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkylamines, alkanolamines, alkylamine oxides, derivatives of protein hydrolysates, hydroxy-mixed ethers, alkyl polyglycosides and alkylglucamides.

Examples of anionic surface-active substances which can be used for combinations and which may be mentioned are: soaps, ether carboxylic acids and salts thereof, alkylsulfonates, α-olefinsulfonates, sulfonates of higher fatty acid esters, alcohol sulfates, alcohol ether sulfates, hydroxy-mixed ether sulfates, salts of phosphate esters, taurides, isethionates, linear alkylbenzenesulfonates, cumenesulfonate, alkylarylsulfonates, sulfates of polyoxyethylene fatty acid amides and salts of acylamino acids.

Examples of customary cationic surface-active substances which can be used for combinations and which may be mentioned are: alkyltrimethylammonium salts, dialkyldimethylammonium salts, alkyldimethylbenzylammonium salts, alkylpyridinium salts, alkylisoquinolinium salts, benzethonium chlorides and cationic acylamino acid derivatives.

Examples of ampholytic surface-active substances which can be used for combinations and which may be mentioned are: amino acids, betaines, sulfobetaines, imidazoline derivatives, soya oil lipids and lecithin.

Furthermore, the amphiphilic compounds according to the invention can also be combined together on their own.

It is likewise possible to add conventional additives to the amphiphilic compounds according to the invention. Such additives are specifically selected for a formulation and normally comprise inorganic salts such as sodium chloride and sulfate, and builders, hydrotropes, UV absorbers, softening agents, chelating agents, viscosity modifiers and fragrances.

The abovementioned compounds can be prepared by known methods:

The dicarboxylic acids or their methyl esters are reacted with two equivalents of amine at elevated temperatures (80 to 240° C.) optimally in the presence of a catalyst, with the water or methanol which is produced being removed under vacuum.

N,N'-Dialkyldicarboxamides are alkoxylated at temperatures from 130 to 190° C. under pressure in the presence of a basic catalyst. This step is optional for dialkylpolyhydroxydicarboxamides (formula XVIII).

The products can subsequently be reacted with $SO_3$/inert gas (oleum, chlorosulfonic acid or sulfamic acid) or polyphosphoric acid or with a haloacetic acid, a sultone, with maleic anhydride and sodium bisulfite or with isethionic acid and be neutralized with aqueous alkali metal or alkaline earth metal hydroxides or ammonia or alkanolamines.

What is claimed is:

1. An amphiphilic compound of the formula (I):

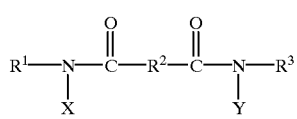
(I)

wherein $R^1$ and $R^3$ are, independently of each other, a branched or unbranched, saturated or unsaturated hydrocarbon radical with 1 to 22 carbon atoms;

$R^2$ is a spacer, which is an unbranched or branched alkylene chain of the formula (II):

(II)

wherein a is from 2 to 18, or an unbranched or branched alkenylene chain of the formula (III):

(III)

wherein b+c is from 2 to 16, where b and c are each greater than 0, or of an unbranched or branched alkynylene chain of the formula (IV):

(IV)

wherein d+e is from 2 to 16, where d and e are each greater than 0, and wherein in the compounds of formulae (II) to (IV), the spacer contains at any desired point in the chain additionally up to four functional side groups, comprising amino, acylamino, carbonyl, carboxyl or hydroxyl, or up to 4 rings, which are isolated or fused, or both; and X and Y are, independently of each other, substituents of the formula (XVI):

(XVI)

wherein α is 0 to 50; β is 0 to 60; and α+β is 1 to 100; wherein $R^2$ is not $C_2H_4$, when β is 0; and wherein with mixed alkoxides, the alkoxide units are incorporated randomly or blockwise and the sequence is arbitrary; or wherein X and Y are, independently of one another, substituents of the formula XVII:

(XVII)

with in each case
γ being 0 to 20,
δ being 0 to 20,
and γ+δ being 1 to 40, where FR is a functional radical —$CH_2$—COOM, —$SO_3$M, —P(O)(OM)$_2$, —O—C(O)=$C_2H_3$ ($SO_3$M)—$CO_2$M', or —$C_2H_4$—$SO_3$M with M, M' being alkali metal, ammonium, alkanolammonium, or ½ alkaline earth metal, or substituents of the formula XVIII:

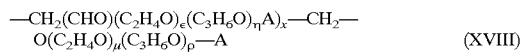
(XVIII)

wherein z is 3 to 6; ε or μ are 0 to 30; and η or ρ are 0 to 30; and where A is H or FR and wherein with mixed alkoxides, the alkoxide units are likewise incorporated randomly or blockwise and the sequence is arbitrary, and wherein at least one of X and Y contains the FR functional radical.

2. The amphiphilic compound of claim 1 wherein the hydrocarbon radicals $R^1$ and $R^3$ in the formula I contain, independently of one another, 7 to 17 carbon atoms.

3. The amphiphilic compound of claim 1 wherein the spacer $R^2$ contains 0 to 20, oxygen or nitrogen atoms or 0 to 4 sulfur atoms or 0 to 3 phosphorus atoms or a combination thereof.

4. The amphiphilic compound of claim 1, wherein α is 10 to 30; β is 20 to 40; and α+β is 10 to 50.

5. The amphiphilic compound of claim 1, wherein z is 4; ε or μ is each 0 to 10; and η or ρ is each 0 to 10.

6. The amphiphilic compound of claim 2, wherein $R^1$ and $R^3$ each have twelve carbon atoms, and $R^2$ is either —$C_2H_4$— or —$C_4H_8$—, and X and Y contain a total of twelve ethylene oxide groups, each having six of said groups, and which further contain —$SO_3$Na functional groups.

7. A method of emulsifying or demulsifying a liquid, which comprises adding one or more of the amphiphilic compounds of claim 1 to said liquid.

8. A method of metal processing, ore production or surface treatment, which comprises effecting said metal processing, ore production or surface treatment with one or more of the amphiphilic compounds of claim 1.

9. A method of cleaning or washing textiles, which comprise cleaning or washing textiles with one or more of the amphiphilic compounds of claim 1.

10. A method of cleaning hand surfaces, which comprises effecting said cleaning with one or more of the amphiphilic compounds of claim 1.

11. A method of cleaning or washing skin or hair or both, which comprises effecting said cleaning or washing with one or more of the amphiphilic compounds of claim 1.

* * * * *

UNITED STATES PATENT AND TRADEMARK OFFICE
CERTIFICATE OF CORRECTION

PATENT NO. : 6,121,482
DATED : September 19, 2000
INVENTOR(S) : Klaus Kwetkat, et al.

It is certified that error appears in the above-identified patent and that said Letters Patent is hereby corrected as shown below:

On the Title Page, Item [54], and Column 1, the Title is incorrect. The Title should read as follows:

--[54] AMPHIPHILIC COMPOUNDS WITH AT LEAST TWO HYDROPHILIC AND AT LEAST TWO HYDROPHOBIC GROUPS BASED ON DICARBOXYLIC ACID DIAMIDES--

Signed and Sealed this

Twelfth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,121,482
DATED : September 19, 2000
INVENTOR(S) : Klaus Kwetkat,- et al.

It is certified that error appears in the above-identified patent and that said Letters Patent is hereby corrected as shown below:

<u>Column 6,</u>
Formula (XVIII), "—$CH_2(CHO)(C_2H_4O)_\epsilon(C_3H_6O)_\eta A)_x$—$CH_2$—$O(C_2H_4O)_\mu (C_3H_6O)_p$—A"
should read
-- —$CH_2(CHO(C_2H_4O)_\epsilon(C_3H_6O)_\eta A)_x$—$CH_2$—$O(C_2H_4O)_\mu (C_3H_6O)_p$—A --;

Line 31, "claim 1 wherein" should read -- claim 1, wherein --;
Line 34, "claim 1 wherein" should read -- claim 1, wherein --.

Signed and Sealed this

Sixth Day of November, 2001

*Attest:*

*Attesting Officer*

NICHOLAS P. GODICI
*Acting Director of the United States Patent and Trademark Office*